(12) United States Patent
Sholev

(10) Patent No.: US 12,611,271 B2
(45) Date of Patent: Apr. 28, 2026

(54) ROBOTIC SURGERY SYSTEM

(71) Applicant: Human Xtensions Ltd., Netanya (IL)

(72) Inventor: Mordehai Sholev, Moshav Amikam (IL)

(73) Assignee: HumanTouch Surgical Ltd, Netanya (IL)

( * ) Notice: Subject to any disclaimer, the term of this patent is extended or adjusted under 35 U.S.C. 154(b) by 125 days.

(21) Appl. No.: 18/282,002

(22) PCT Filed: Mar. 15, 2022

(86) PCT No.: PCT/IL2022/050292
§ 371 (c)(1),
(2) Date: Sep. 14, 2023

(87) PCT Pub. No.: WO2022/195588
PCT Pub. Date: Sep. 22, 2022

(65) Prior Publication Data

US 2024/0138944 A1     May 2, 2024

Related U.S. Application Data

(60) Provisional application No. 63/160,965, filed on Mar. 15, 2021.

(51) Int. Cl.
*A61B 34/37*     (2016.01)
*A61B 1/00*     (2006.01)
(Continued)

(52) U.S. Cl.
CPC .............. *A61B 34/37* (2016.02); *A61B 34/25* (2016.02); *A61B 2034/256* (2016.02); *A61B 2034/305* (2016.02)

(58) Field of Classification Search
CPC ... A61B 34/37; A61B 34/25; A61B 2034/256; A61B 2034/305; A61B 2017/00212;
(Continued)

(56) References Cited

U.S. PATENT DOCUMENTS

2011/0174861 A1* 7/2011 Shelton, IV ..... A61B 17/07207
227/175.1
2013/0245375 A1 9/2013 DiMaio
(Continued)

FOREIGN PATENT DOCUMENTS

CN     102596086 A * 7/2012 ............. G06F 3/014
CN     102834064     12/2012
(Continued)

OTHER PUBLICATIONS

International Preliminary Report on Patentability Dated Sep. 28, 2023 From the International Bureau of WIPO Re. Application No. PCT/IL2022/050292 (7 Pages).
(Continued)

*Primary Examiner* — Harry Y Oh

(57)     ABSTRACT

A surgical system having a surgical device with an integrated user interface controllable by a hand of a surgeon, an adaptor for connecting the integrated user interface of the surgical device to a robotic arm and a control unit for remotely operating the surgical device when connected to the robotic arm.

7 Claims, 12 Drawing Sheets

(51) Int. Cl.

| | |
|---|---|
| *A61B 17/00* | (2006.01) |
| *A61B 34/00* | (2016.01) |
| *A61B 34/30* | (2016.01) |
| *A61B 34/35* | (2016.01) |
| *A61B 90/00* | (2016.01) |
| *A61B 90/50* | (2016.01) |

(58) Field of Classification Search
CPC .......... A61B 2017/00477; A61B 34/70; A61B 1/00149; A61B 2034/2059; A61B 2034/302; A61B 34/30; A61B 2017/00221; A61B 2090/065; A61B 2090/508; A61B 34/35; A61B 90/50
See application file for complete search history.

(56) References Cited

U.S. PATENT DOCUMENTS

| | | |
|---|---|---|
| 2014/0222023 A1 | 8/2014 | Kim et al. |
| 2016/0249993 A1 | 9/2016 | Farahmand et al. |
| 2019/0021801 A1 | 1/2019 | Radgowski et al. |
| 2020/0289216 A1 | 9/2020 | Denlinger et al. |
| 2021/0045819 A1 | 2/2021 | Castillo et al. |
| 2022/0104807 A1 * | 4/2022 | Shelton, IV ......... A61B 17/072 |

FOREIGN PATENT DOCUMENTS

| | | | | |
|---|---|---|---|---|
| JP | 2014-517708 | | 7/2014 | |
| JP | 2023503997 A | * | 2/2023 | ...... A61M 25/09041 |
| WO | WO 2007/038998 | | 4/2007 | |
| WO | WO 2016/136318 | | 9/2016 | |
| WO | WO 2019/186563 | | 10/2019 | |
| WO | WO 2022/195588 | | 9/2022 | |

OTHER PUBLICATIONS

International Search Report and the Written Opinion Dated Jul. 27, 2022 From the International Searching Authority Re. Application No. PCT/IL2022/050292. (23 Pages).

Invitation to Pay Additional Fees Dated Jun. 2, 2022 From the International Searching Authority Re. Application No. PCT/IL2022/050292. (2 Pages).

Supplementary European Search Report and the European Search Opinion Dated Apr. 11, 2025 From the European Patent Office Re. Application No. 22770762.7. (13 Pages).

Communication Pursuant to Rule 164(1) EPC: Supplementary Partial European Search Report and the European Provisional Opinion Dated Jan. 21, 2025 From the European Patent Office Re. Application No. 22770762.7. (15 Pages).

Notice of Reason(s) for Rejection Dated Oct. 14, 2025 From the Japan Patent Office Re. Application No. 2023-555315 and Its Translation Into English. (14 Pages).

* cited by examiner

ROBOTIC SURGERY SYSTEM

RELATED APPLICATIONS

This application is a National Phase of PCT Patent Application No. PCT/IL2022/050292 having International filing date of Mar. 15, 2022, which claims the benefit of priority under 35 USC § 119(e) of U.S. Provisional Patent Application No. 63/160,965 filed on Mar. 15, 2021. The contents of the above applications are all incorporated by reference as if fully set forth herein in their entirety.

FIELD AND BACKGROUND OF THE INVENTION

The present invention relates to a system for robotic surgery and, more particularly, to a handheld surgical device couplable to a robotic arm and operable via a remote-control unit.

Robotic devices are increasingly being used to assist surgeons in surgical procedures. Such robotic devices are not designed to replace the surgeons but rather as collaborative robots.

Collaborative robots (cobots) typically include a moveable arm (robotic arm) having a maneuverable distal end to which a surgical instrument can be attached. An operator can precisely position the arm and the attached surgical instrument at an anatomical site to perform a medical or surgical procedure. One of the more familiar cobots is the da Vinci System, built with robot arms and high-tech cameras to assist surgeons during operations. The da Vinci's arms translate surgeon hand movements into smaller, more precise movements, allowing for less invasive procedures.

Precise control of the robotic arm is crucial to both safety and success of a medical procedure. Typical robotic systems have one of three control modes: passive control in which the robot is operated manually, active control in which the robot can move autonomously according to a pre-programmed trajectory and tele-control in which the robot is controlled by a remote operator.

One advantage of using a robotic system is that the system arm, unlike the arms and hands of a surgeon, are not subjected to muscle strain or neurological actions like twitching. Thus, using a medical robotic system it is possible to hold an instrument steady, or move the instrument along a defined path with a higher degree of accuracy.

While robotic surgical systems provide numerous benefits, surgical steps, like extensive or complex suturing, oftentimes require switching between manual and robotic surgery.

There thus remains a need for a robotic surgical system that enables the surgeon to seamlessly and rapidly switch between robotic and manual surgery thus leveraging the benefits of each approach when and where suitable.

SUMMARY OF THE INVENTION

According to one aspect of the present invention there is provided a surgical system comprising a surgical device having an integrated user interface controllable by a hand of a surgeon; an adaptor for connecting the surgical device to the integrated user interface; and a control unit for remotely operating the surgical device and the robotic arm, wherein remote control of the surgical device dictates movements of the robotic arm.

According to embodiments of the present invention when the adaptor is connected to the surgical device the integrated user interface is converted into a passive coupler to the robotic arm.

According to embodiments of the present invention the passive coupler provides orientation information for the robotic arm when the adaptor is coupled to the integrated user interface.

According to embodiments of the present invention a control of the surgical device end effector is transferred to the remote control unit when the adaptor is connected to the integrated user interface.

According to embodiments of the present invention the adaptor is connectable to or integrated with the robotic arm.

According to embodiments of the present invention the rod fits into a slot in the integrated user interface, the slot being in a center of rotation of the integrated user interface.

According to embodiments of the present invention fitting the rod into the slot activates a switch for transferring control of the integrated user interface to the control unit.

According to embodiments of the present invention the adaptor externally connects to the integrated user interface.

According to embodiments of the present invention the adaptor is configured for attachment to the integrated user interface over a sterile drape.

According to embodiments of the present invention when the adaptor is connected to the surgical device the integrated user interface is mechanically locked.

According to one aspect of the present invention there is provided a medical device comprising a control unit including an integrated user interface having a palm interface mounted on a pivotal support attached to a housing of the control unit, the palm interface being tiltable to operate the medical device, the palm interface being configured for attachment to a robotic arm such that when attached, the palm interface is locked in a center position and is incapable of operating the medical device.

According to embodiments of the present invention the pivotal support is gimbaled.

According to embodiments of the present invention the medical device includes a shaft having a steerable portion and further wherein manual tilting of the palm interface deflects the steerable portion of the medical device.

According to embodiments of the present invention the palm interface includes a slot for accepting a rod attached to the robotic arm.

According to embodiments of the present invention the slot is keyed for orientation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE SEVERAL VIEWS OF THE DRAWING(S)

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figures 3A, 3B:
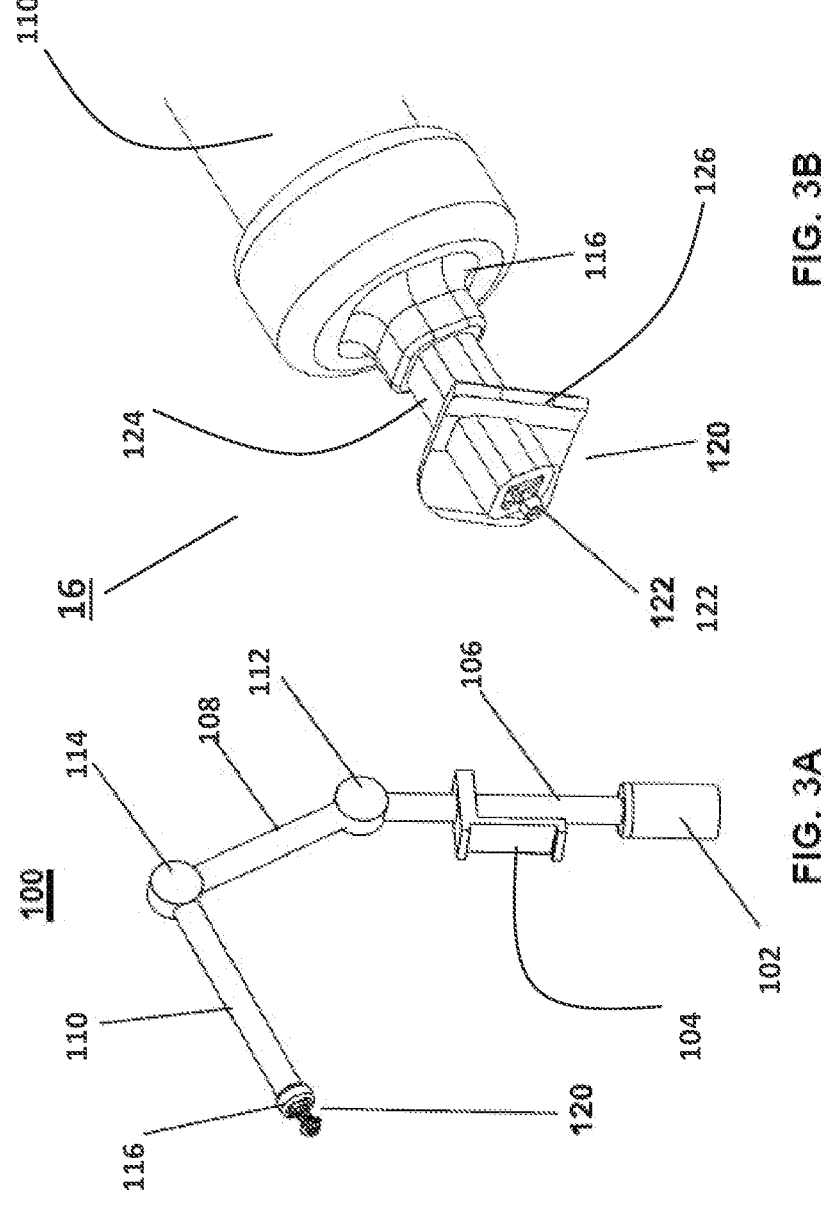

FIGS. 3A-B illustrate the robotic arm (FIG. 3A) and the adaptor portion (FIG. 3B) for connecting to the handheld surgical instrument.

Figure 4:
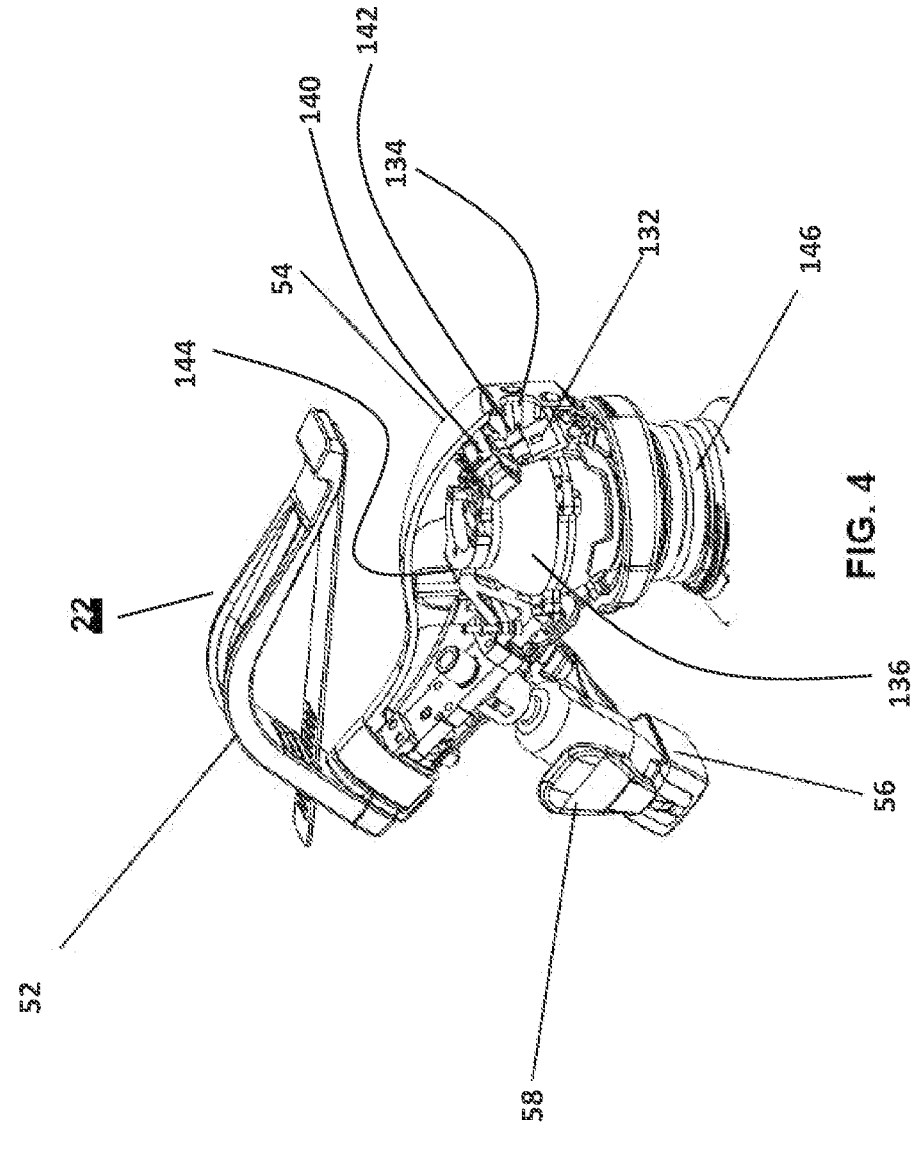

FIG. 4 illustrates in greater detail the integrated user interface of the handheld surgical instrument showing the internal components and the adaptor connection site of the integrated user interface.

Figure 5:
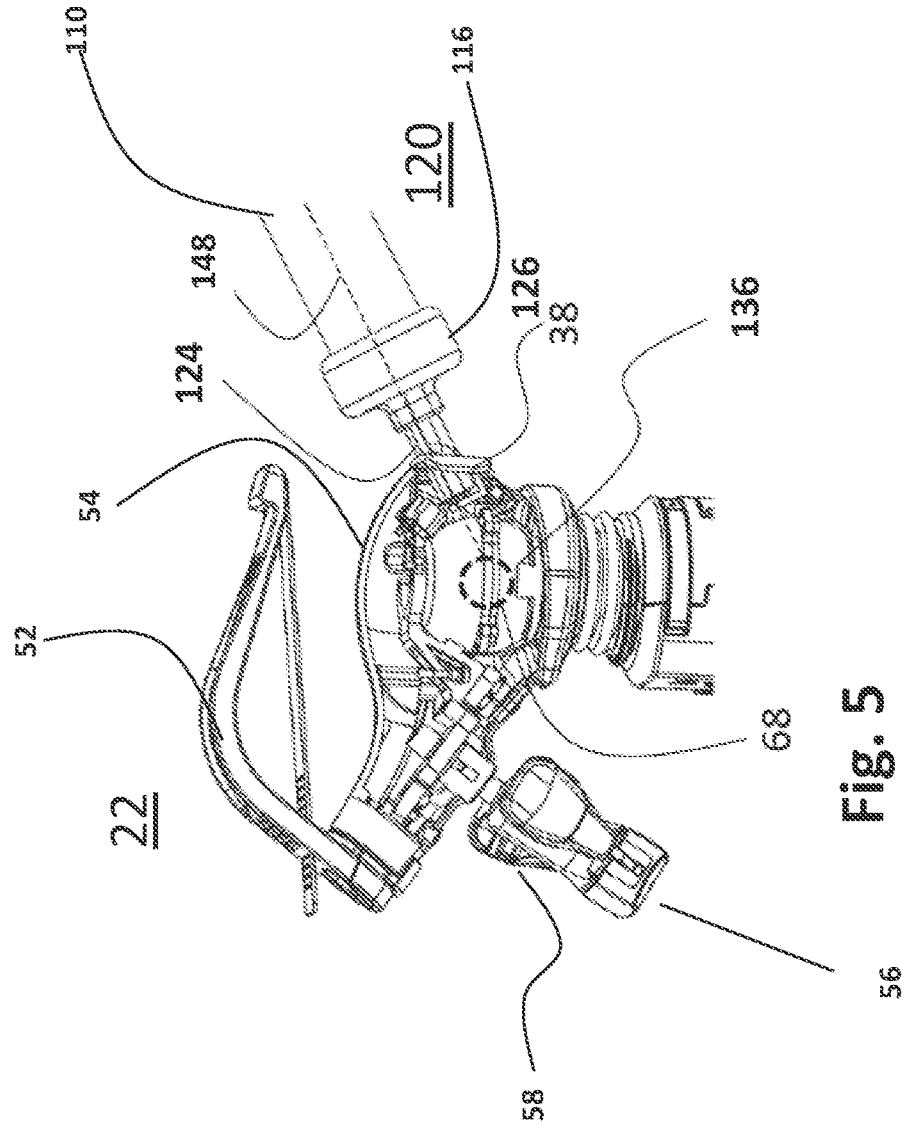

FIG. 5 illustrates the connection between the adaptor of the robotic arm and the integrated user interface.

Figure 6:
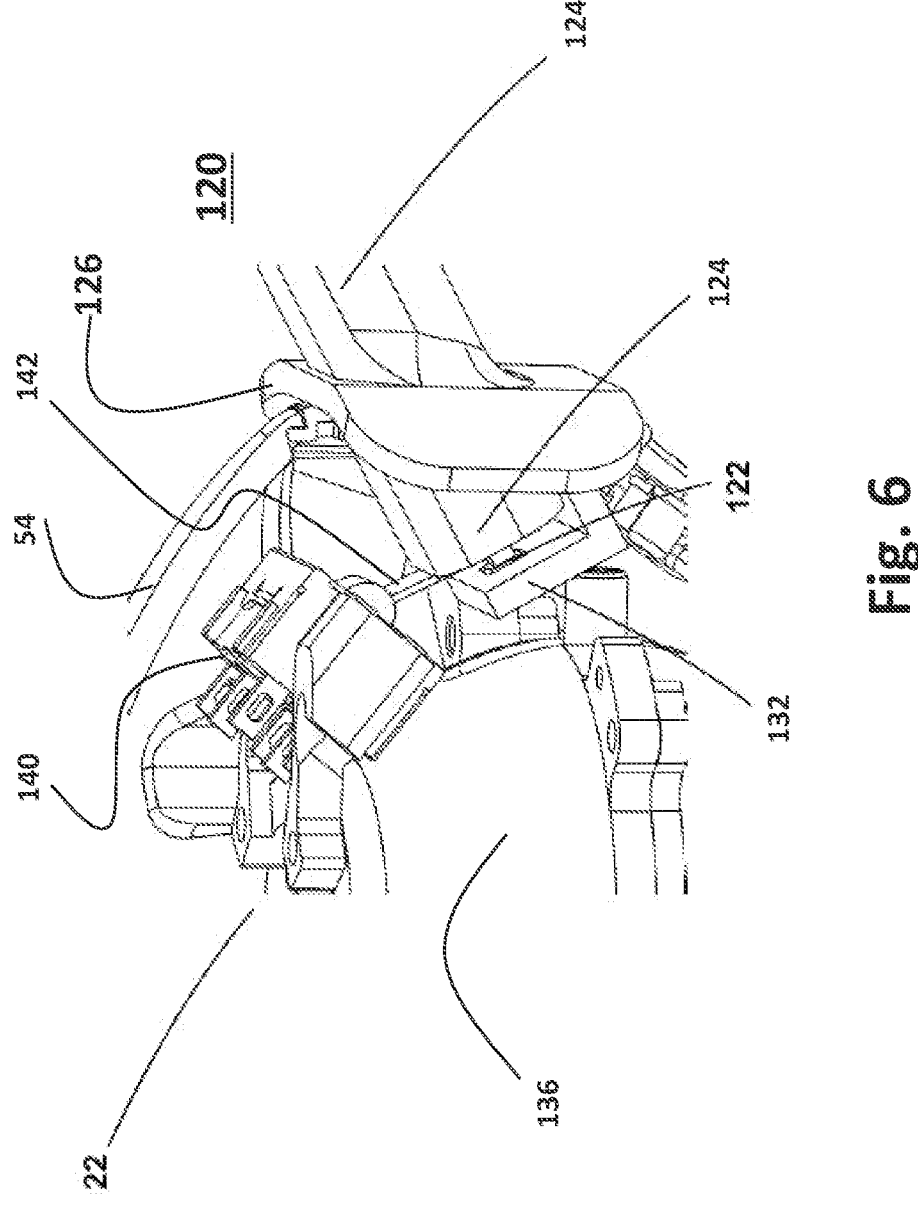

FIG. 6 illustrates the adaptor connection to the integrated user interface and the rod for maintaining the integrated user interface centered when connected to the robotic arm.

FIGS. 7A-E illustrate the movement of the handheld surgical instrument and its deflectable tip when operated manually via the integrated user interface (FIG. 7A) and remotely via the remote user interface operating the handheld surgical instrument when connected to the robotic arm (FIGS. 7B-E).

Figures 7A, 7B, 7C, 7D, 7E, 7F:
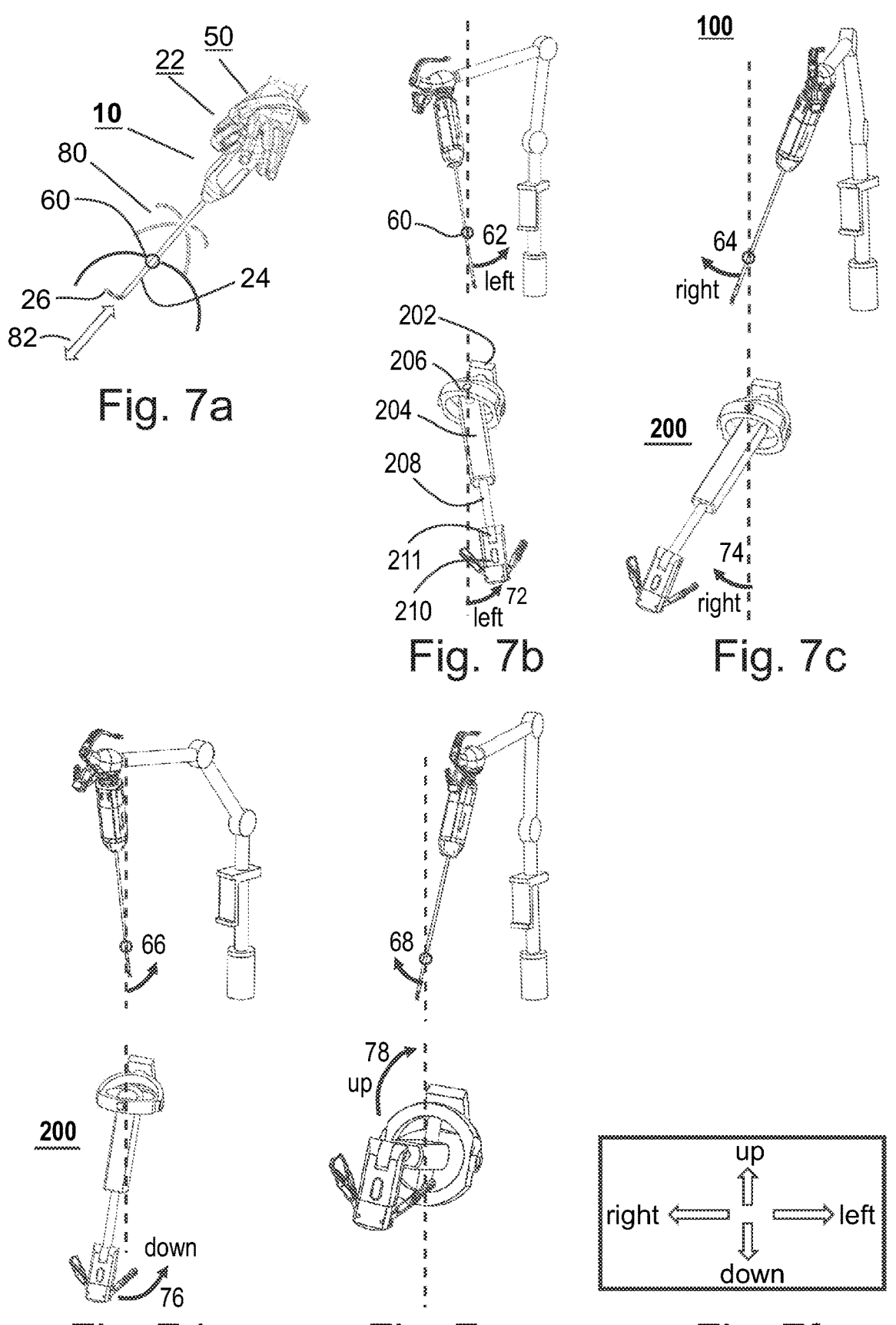

FIG. 7F illustrates the direction of motion as observed by the surgeon on a screen.

Figures 8A, 8B:
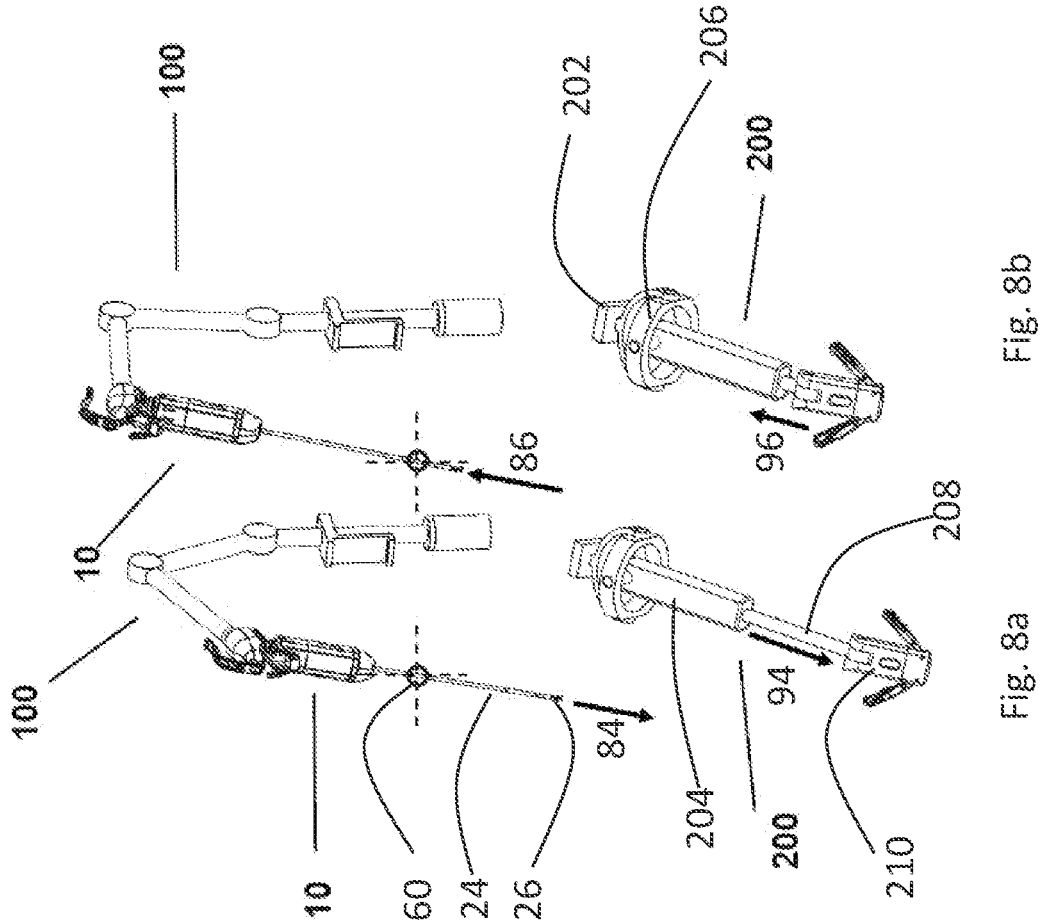

FIGS. 8A-B illustrate the surgical tool advance and retract motion as operated by the remote user interface and robotic arm.

Figures 9A, 9B:
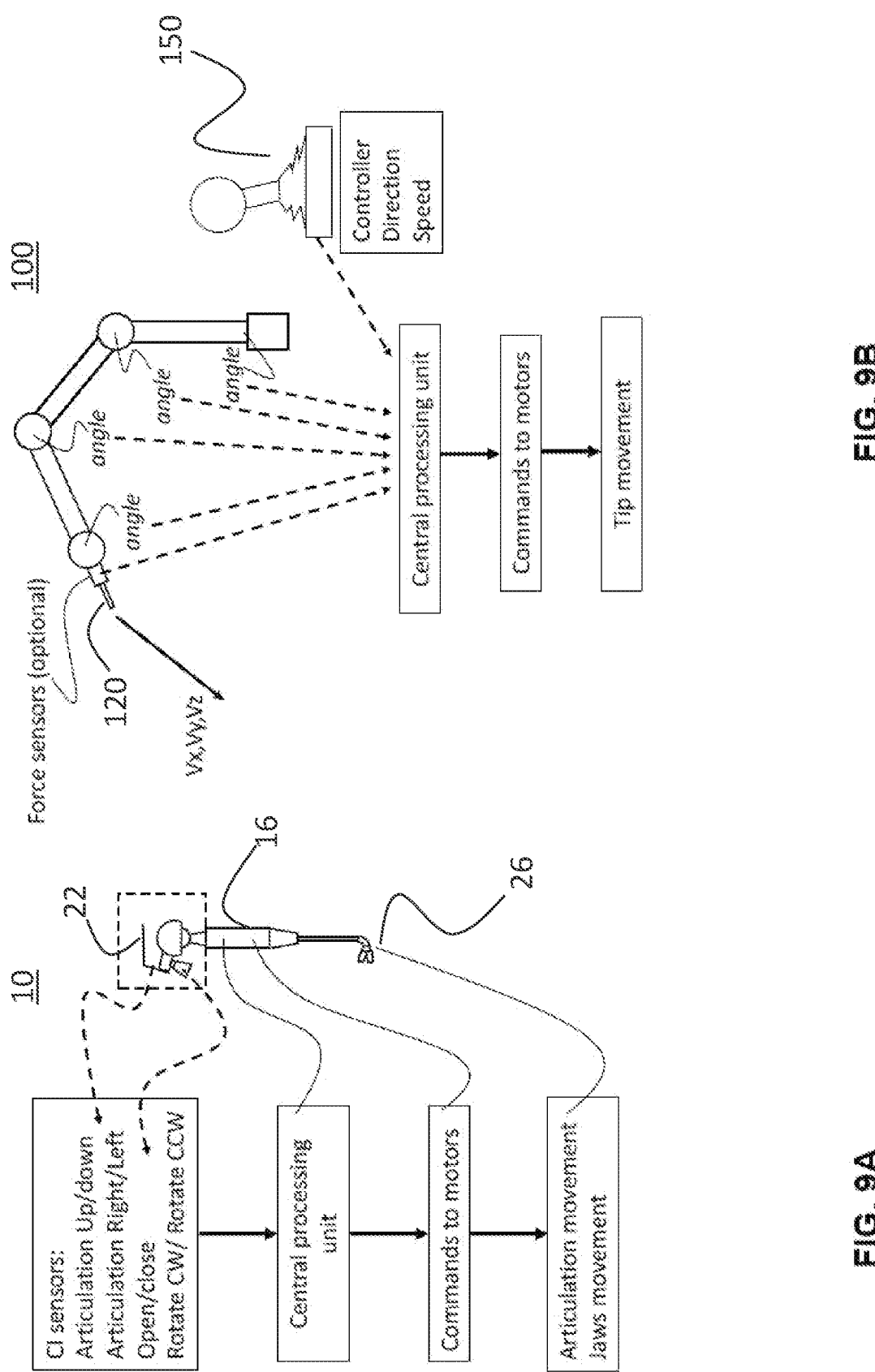

FIGS. 9A-B illustrate the processing steps for controlling the surgical instrument when movement is actuated via the integrated user interface (FIG. 9A) and the remote user interface and robotic arm (FIG. 9B).

Figure 10:
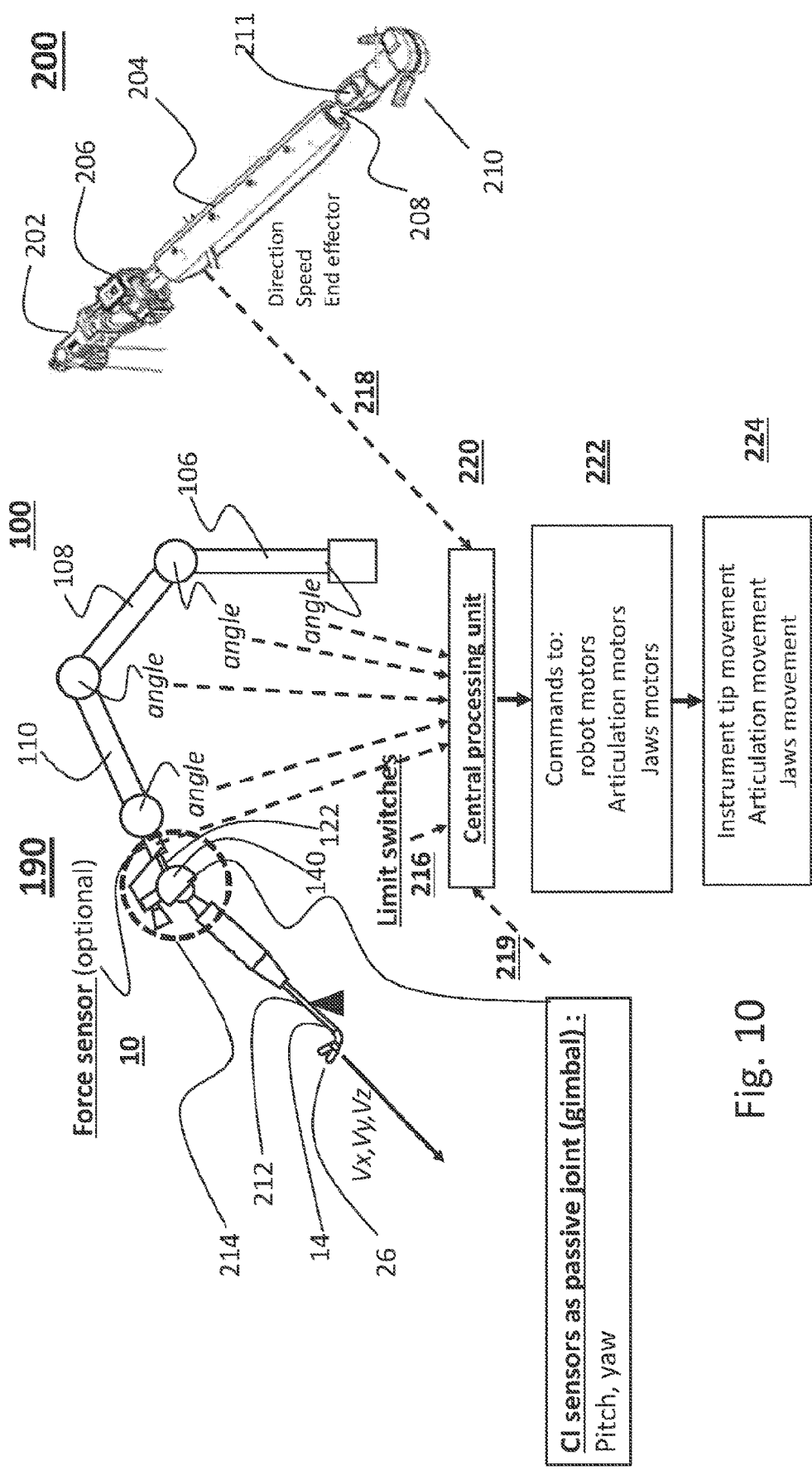

FIG. 10 illustrates the measurement from sensors serving as feedback for control over the robotic arm via the remote user interface.

Figure 11:
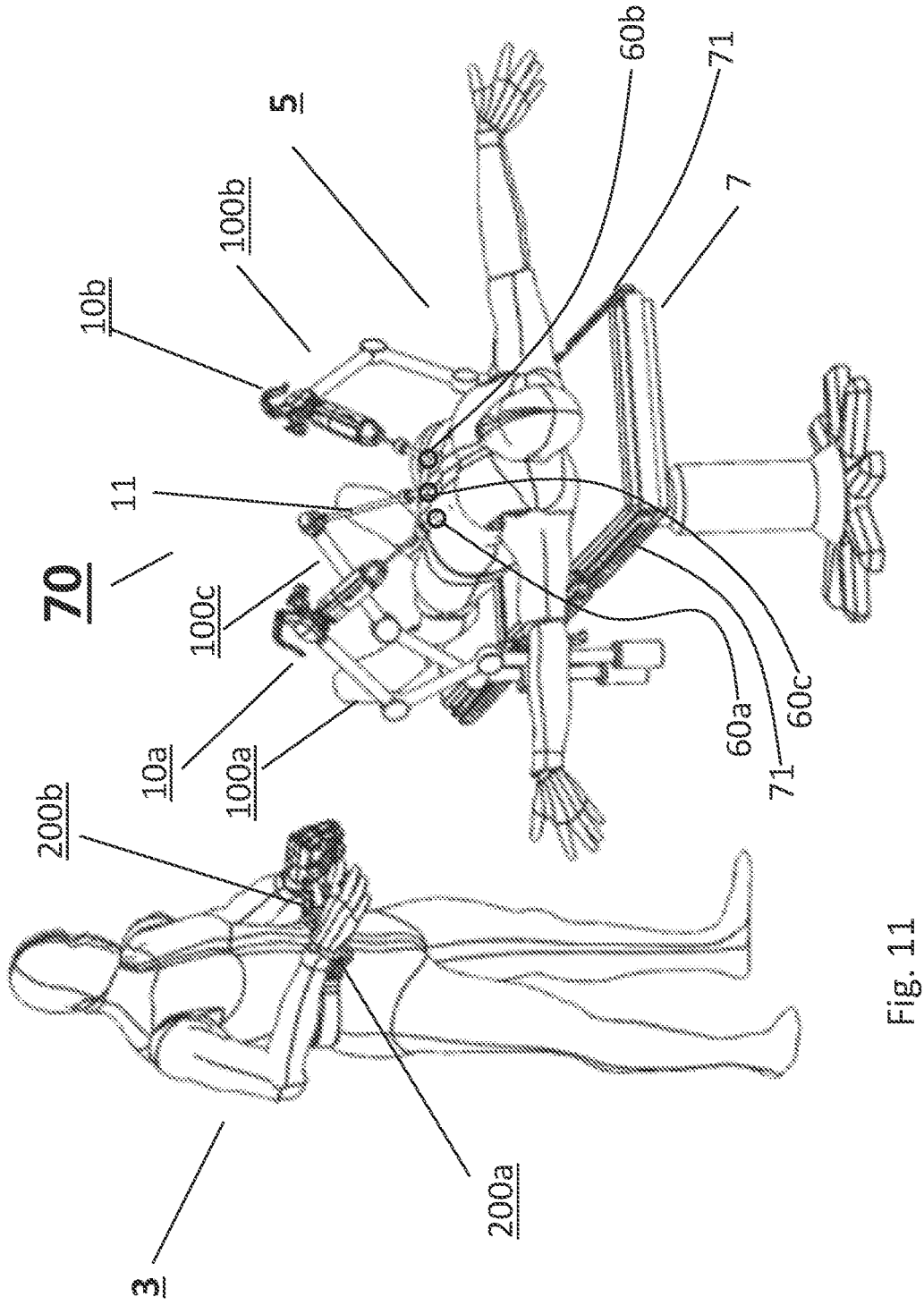

FIG. 11 illustrates a surgeon controlling several robotic arms and attached surgical devices via a single remote interface.

FIGS. 12A-F illustrate adapters configurations suitable for connecting the robotic arm to a draped handheld device.

DESCRIPTION OF SPECIFIC EMBODIMENTS OF THE INVENTION

The present invention is of a system which can be used for manual and robotic surgery. Specifically, the present invention can be used to provide a surgeon with both manual and robotic surgical capabilities using a single surgical system.

The principles and operation of the present invention may be better understood with reference to the drawings and accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

Typical robotic systems have one of three control modes: passive control in which the robot is operated manually, active control in which the robot can move autonomously according to a pre-programmed trajectory and tele-control in which the robot is controlled by a remote operator.

Although robotic surgical systems allow precise control over surgery and enhance the safety and success of a medical procedure, they are typically dedicated systems in which the surgical instrument is designed specifically for attachment to, or integration with, the robotic arm and thus cannot be used manually in case of system failure, or when the surgeon wishes to operate the surgical instrument while the surgical instrument is not connected to the robotic arm.

While reducing the present invention to practice, the present inventor have devised a surgical system that is capable of providing both robotic and manual operating modes.

Thus, according to one aspect of the present invention there is provided a surgical system that can be used in open or minimally invasive procedures. The surgical system includes a surgical device having an integrated user interface controllable by a hand of a surgeon and an adaptor for connecting the surgical device to a robotic arm through the integrated user interface. The surgical device having an integrated user interface can be operated manually through hand control over its integrated user interface but when connected to the robotic arm through the adaptor, the surgical device is controlled via a remote user interface (e.g., that is attached to the surgeon). Thus, adaptor coupling effectively converts the integrated user interface into a passive coupler. The remote user interface controls the surgical device (in a manner similar to that of the integrated user interface) and thus dictates movement of the robotic arm. Remote control over the operation of the end effector of the surgical device (e.g., operating device articulation, operation of a grasper attached thereto etc.) is not relayed through the integrated user interface of the surgical device, but transferred directly to the device controller and utilizes position/force sensors integrated into the surgical device or the adaptor. Remote control over the spatial position of the surgical device is relayed through the robotic arm and utilizes position/force sensors integrated into the robotic arm, adaptor and optionally those integrated into the surgical device.

This configuration and functionality of the present system enables a surgeon to manually operate the surgical device when detached from the robotic arm and to robotically control the same instrument when attached to the robotic arm in a manner similar to open surgery where the need to use a fulcrum is eliminated.

This enables a surgeon having experience with manually controlling a surgical device to quickly adapt to operating the same device through a robotic arm setup.

The adaptor can form a part of the robotic arm (or the integrated user interface). In any case, the adaptor can include a rod (or pin) that connects to a housing that preferably is co-aligned with the center of rotation of the integrated user interface thus locking the integrated user interface in a set position. Connecting the rod into the housing activates limit switches that transfer control from the integrated user interface of the surgical device to the control unit.

The robotic arm can be any type of arm having one, two, three or more joints that are capable of movement in one or more planes.

Unlike the present robotic surgery applications in which robots are isolated from human contact, collaborative robots (or Cobots) are designed to work collaboratively with humans in confined spaces and as such are designed for safety with lightweight construction, rounded edges, and inherent limitation on speed and force, while utilizing sensors and software that ensure safe operation.

The Cobot and human may work in the same area at the same time, while the human and cobot are both in motion, and the cobot responds in real-time to human movement.

A typical Cobot arm includes several individual arm sections interconnected by joint. Each arm can include motors, a brake system and sensors. The joints and arms are connected to central control system for controlling the motors and the braking system of each joint and receiving and processing sensors signals. Each joint includes a housing with input and output members.

The input member of the joint housing is connected to the distal end of a link proximal to the joint. The output member of the housing is rotatable relative to the housing by the motor mounted in the housing. The joint housing can also contains a safety brake. The safety brake typically includes an annular member mounted on the motor axle, whereby the annular member rotates relative to the motor axle, but with friction between the annular member and the motor axle. The braking mechanism can also include a solenoid, which upon activation of the brake, displaces a ratchet into engagement with the annular member to slow the rotation of motor axle relative to the housing.

The joint housing can also include two encoders as part of the sensors. The first encoder senses an angular orientation of the output member relative to the housing, and the second encoder senses the angular orientation or rotation of the motor axle relative to the joint housing.

Each Cobot arm system also includes a proximal base that may be connected to a cart, working surface, or a clamp and a distal connector. The distal connector allows attachment of end effectors, camera, or additional sensors which are configured to be specifically used with a Cobot.

A central control circuit can be integral with the cobot arm system or may be placed in an external box.

There are numerous types of commercial cobots available on the market. The cobots system may vary in their dimensions, weight, reach, general envelope of motion, power consumption, pay load, accuracy, noise, and adaption to different environment conditions such as dust, humidity, and temperature.

For example: a small collaborative table-top Cobot, such as UR3e for light assembly tasks and automated workbench scenarios, may weighs 11 kg, with a payload of 3 kg, with reach of 0.5M and ±360-degree rotation on all wrist joints, and infinite rotation on the end joint.

A heavy duty Cobot such as UR16e, for use in heavy machine tending, material handling, packaging, and screw and nut driving applications, may weighs 33 kg, with a payload of 16 kg (35.3 lbs.) with reach of 0.9M and ±360-degree rotation on all wrist joints, and infinite rotation on the end joint.

In the field of laparoscopic surgery, the Cobot may have the ability to carry a payload of at least 1 Kg with a reach of at least 0.4M. The robotic arm can have at least 3 motorized degrees of freedom and a weight that does not exceed 15 Kg. A cobot can be fixed or clamped to the surgical table or attached to carts.

Cobots that can be modified for use with the present invention include the KINOVA-MICO2: 6 axis cobot that can carry a payload of 2.1 kg, with reach of 0.7M, and weights 4.6 kg, the UNIVERSAL ROBOTS-UR3, a 6 axis cobot that can carry a payload of 3 kg, with reach of 0.5M, and weights 11 kg or the UR3 cobot manufactured by UNIVERSAL ROBOTS.

The surgical device can be any type of motorized device that is operated manually via arm and hand movements. Such a device can be configured for minimally invasive surgery through an access port (trocar). The surgical device can include a control unit attached to a shaft having an end effector (grasper, cutter, camera etc.). The user interface can control shaft deflection/articulation (through wires or motors and wires/gears) as well as the operation of the effector end (e.g., grasper). Spatial positioning of the surgical device (up/down, side-to-side) can be controlled by arm movements. An example of a surgical device configured for use with the present system is described hereinbelow.

The remote user interface can be similar in function to the integrated user interface in that it provides similar controls over shaft deflection and effector end operation while also providing user controls for spatial positioning (carried out by the robotic arm). An example of a remote user interface configured for use with the present system is described hereinbelow.

Figures 1, 2:
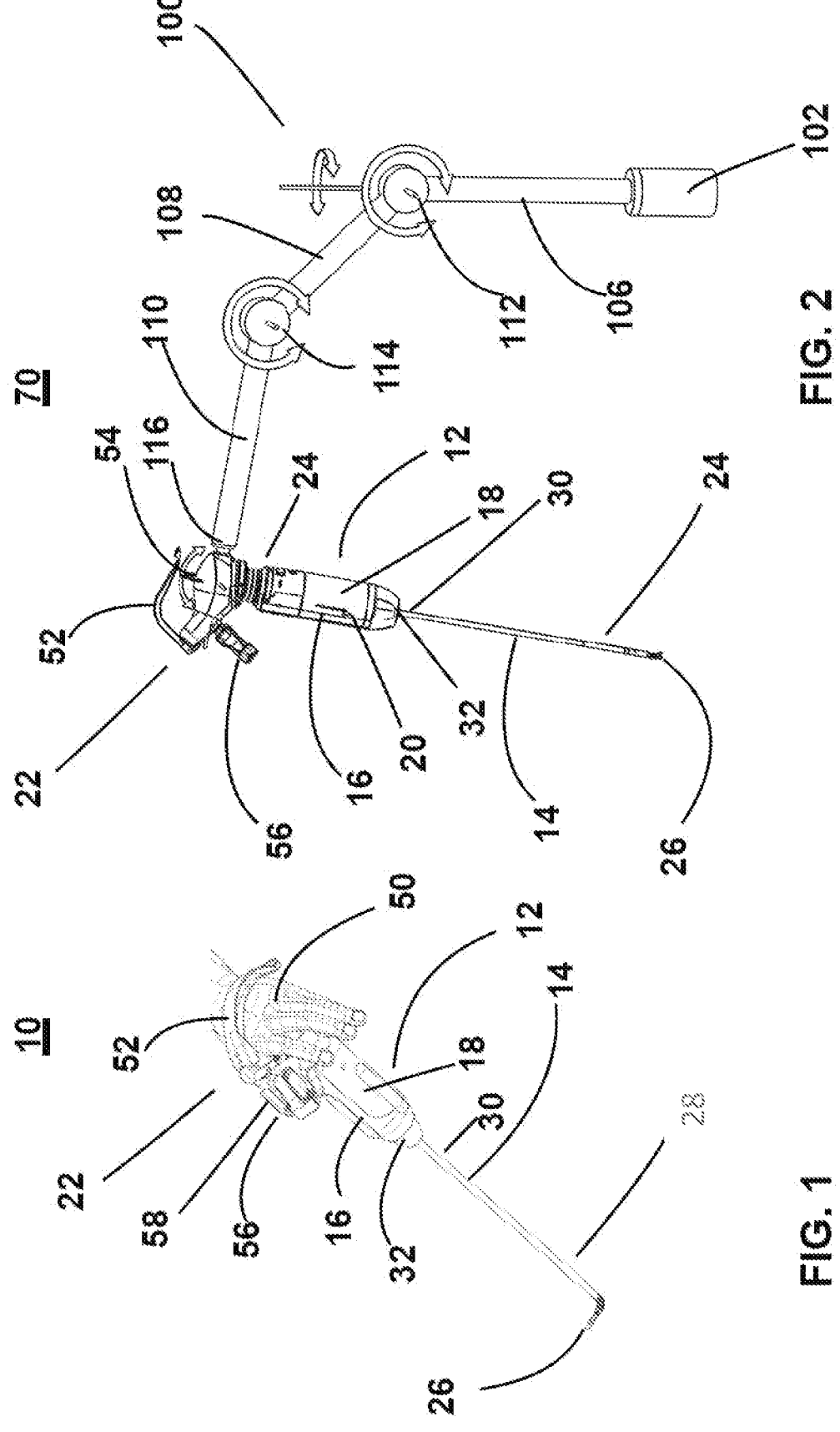
FIG. 1 illustrates a handheld surgical instrument having an integrated user interface controllable by a hand of a user.
FIG. 2 illustrates the handheld surgical instrument of FIG. 1 attached to a robotic arm configured in accordance with the teachings of the present invention.

Referring now to the drawings, FIGS. 1 and 2 illustrate a manually operable surgical device and a robotic arm fitted with the surgical device (respectively).

The surgical device (referred to hereinunder as device 10) includes a control unit 22 attached to a shaft 14.

Control unit 22 includes a housing 16 which contains a drive unit 18 circuitry 20 and an integrated user interface 22 (hereinafter interface 22) which is mounted on a proximal end 24 of housing 16. Housing 16 and interface 22 can be fabricated from a polymer and/or alloy using machining, 3D printing and/or casting/molding fabrication approaches. Housing 16 can be 40-60 mm in diameter and about 60-150 mm in height. Interface 22 is also shown in FIGS. 4-5.

Shaft 14 can include a steerable portion 24 and a distally mounted end effector end/instrument (grasper 26 shown). Shaft 14 can be fabricated using materials and approaches well known in the art.

Shaft 14 includes a plurality of wires disposed along its length for transferring force from drive unit 18 to an end of steerable portion 28 and jaws 26.

Shaft 14 can be 20-40 cm in length and 3-16 mm in diameter and can be hollow or solid. A hollow shaft 14 enables internal routing of wires, in a solid configuration of shaft 14, wires can be routed on the external surface of shaft 14 through dedicated guides.

The steerable portion of shaft 14 can be fabricated from a tube having cutouts (e.g. such as those shown in U.S. Pat. No. 4,911,148) or from links (e.g. U.S. Pat. Nos. 7,682,307, 6,817,974) with control wires running through guides formed in the tube or links. Alternatively, the steerable portion can be fabricated as described in U.S. Provisional Patent Application No. 61/765,745 to the present inventor, the teachings of which are fully incorporated herein.

Proximal end 30 of shaft 14 is attached to a distal end 32 of housing 16, and control and actuation wires/rods of shaft 14 run through housing 32 and attach to drive unit 18. Drive unit 18 can include levers and gears for translating movements of user interface 22 to pulling of control and/or actuation wires. Such transfer can be mechanical (manual) or motorized.

The surgeon's hand 50 is placed in such a manner where the back of the user's hand is positioned under restraint 52 while three of the user's fingers are free to grasp a palm interface 54, the thumb and index fingers engage a finger interface 56.

Restraint 52 is elastically deformable to conform to back of the surgeon's hand while applying a downward force thereto.

Palm interface 54 is pivotally attached to a base which includes sensors for measuring the spatial orientation of the user's hand, by measuring the orientation of palm surface 54 with respect to the base.

Finger interface 56 is connected to palm interface 54. Additionally, paddles 58 of finger interface 56 (two are shown) are movable (pinched inward, released outward) and rotatable (clock wise, counter clock wise) to control an effector end (e.g. surgical tool such as grasper) of device 10.

As is shown in FIG. 2, device 10 is connectable to a robotic arm 100 through interface 22 (collectively, referred to herein as system 70). Robotic arm 100 includes a base 102 for connecting robotic arm 100 to a bed, table or the like, and 3 segments (106, 108, 110) interconnected via joints (112, 114). A joint 116 connects robotic arm 100 to device 10 via an adaptor (described hereinbelow).

FIGS. 3A-B illustrate robotic arm 100 and adaptor 120 with rod 124 for connecting robotic arm 100 to surgical device 10 through interface 22.

FIG. 3A is a general view of robotic arm 100 with adaptor 120 located at the distal end of the distal link 110. In this configuration, robotic arm 100 includes 3 links: vertical link 106 that rotates around its longitudinal axis relative to base 102, segment 108 that is connected to segment 106 via joint 112 (part of motor housing) and distal segment 110 that is connected to segment 108 via joint 114 (part of motor housing). Segments 108 and 110 rotate around the longitudinal axis of joints 112 and 114. It should be noted that in FIG. 3A, robotic arm 100 has the minimal number of arms and joints to enable robotic arm 100 to spatially locate adaptor 120 at any desired position. Various robotic arms and Cobots are available in the market offering various number of segments and joints. Robotic arm 100 can be fabricated by modifying a commercially available cobot to include distal adapter 120. Clamp 104 may be used for connecting robotic arm 100 to cart or surgical table. The length of segments 108 and 110 may be 20-40 cm allowing a reach of 40-80 cm.

FIG. 3B illustrates adaptor 120 in greater detail. Adaptor 120 connects the distal end of link 110 of robotic arm 100 preferably to the center of rotation of user interface 22 of device 10. Adaptor 120 is connected to distal end of arm 110 via ring adapter 116. Rod 124 projects out of ring 116 and has a keyhole (asymmetrical shape) allowing a single orientation of connection to interface 22 of device 10. Limit switch 122 on the distal end of rod 124 is depressed when rod 124 is fully connected to user interface 22. Bulge 126 interfaces with the external surface 54 of user interface 22 and functions as a support when robotic arm 100 carries device 10.

FIG. 4 is a cut-away view showing in greater detail the inner structure of user interface 22 and connector housing 132 for connecting with robotic arm 100 through adapter 120. Limit switch 140, located at user interface 22 of device 10. Lever 142 of limit switch 140 indicates if rod 124 of adapter 120 is clicked into connector housing 132. User interface 22 includes palm interface 54 covering a spherical base 136 that allows the user to tilt user interface 22 with respect to the body 16 of device 10, around the center of spherical base 136. Spherical base 136 is connected to palm interface 54 via frame 144. Palm interface 54 includes an opening 134 that allows rod 124 of adapter 120 to mechanically connect to spherical base 136, at a center thereof. When rod 124 is secured to housing 132 lever 142 of limit switch 140 is depressed indicating that the robotic arm 100 is connected to handheld device 10.

FIG. 5 is a cut-away view showing the connection between adaptor 120 of the robotic arm 100 and user interface 22 of device 10. Rod 124 is connected to housing 132, while center line 148 of rod 124 co-aligned with the longitudinal axis of link 110 is directed to the center of rotation 148 of spherical base 136 (as is indicated by dashed circle 68). When rod 124 is clicked into housing 132, switch 122 (shown in FIG. 3B) is depressed against housing 132 and lever 142 of limit switch 140 is depressed by rod 124.

FIG. 6 illustrates in greater detail the connection between adaptor 120 of the robotic arm 100 and user interface 22 of device 10. Rod 124 of adaptor 120 (passing through keyhole shaped opening 134) is clicked into housing 132 located in interface 22 thereby depressing switch 122 against housing 132 while lever 142 of limit switch 140 is depressed by rod 124; bulge 126 supports cover 130 of interface 22.

As is further described hereinbelow with respect to FIGS. 9A-10, when both limit switches 122 and 140 are depressed the separate control systems of handheld motorized device 10 and robotic arm 100 unite under a single control circuit, enabling the surgeon to control simultaneously the end effector 26 of handheld motorized device 10 and robotic arm 100.

FIGS. 12A-F illustrate an adaptor suitable for connecting a robotic arm to a draped device.

In cases where device 10 is draped (for sterility reasons) an external adaptor configuration is needed in order to connect robotic arm 100 to device 10. Adaptor 300 includes arms 302 that grip the external surface of interface 22. When interface 22 is draped, arms 302 firmly grip interface 22 without interrupting the sterile barrier provided by the drape. Adapter 300 can include a limit switch 122 that indicates if adapter 310 is connected to interface 22.

Figures 12A, 12B, 12C:
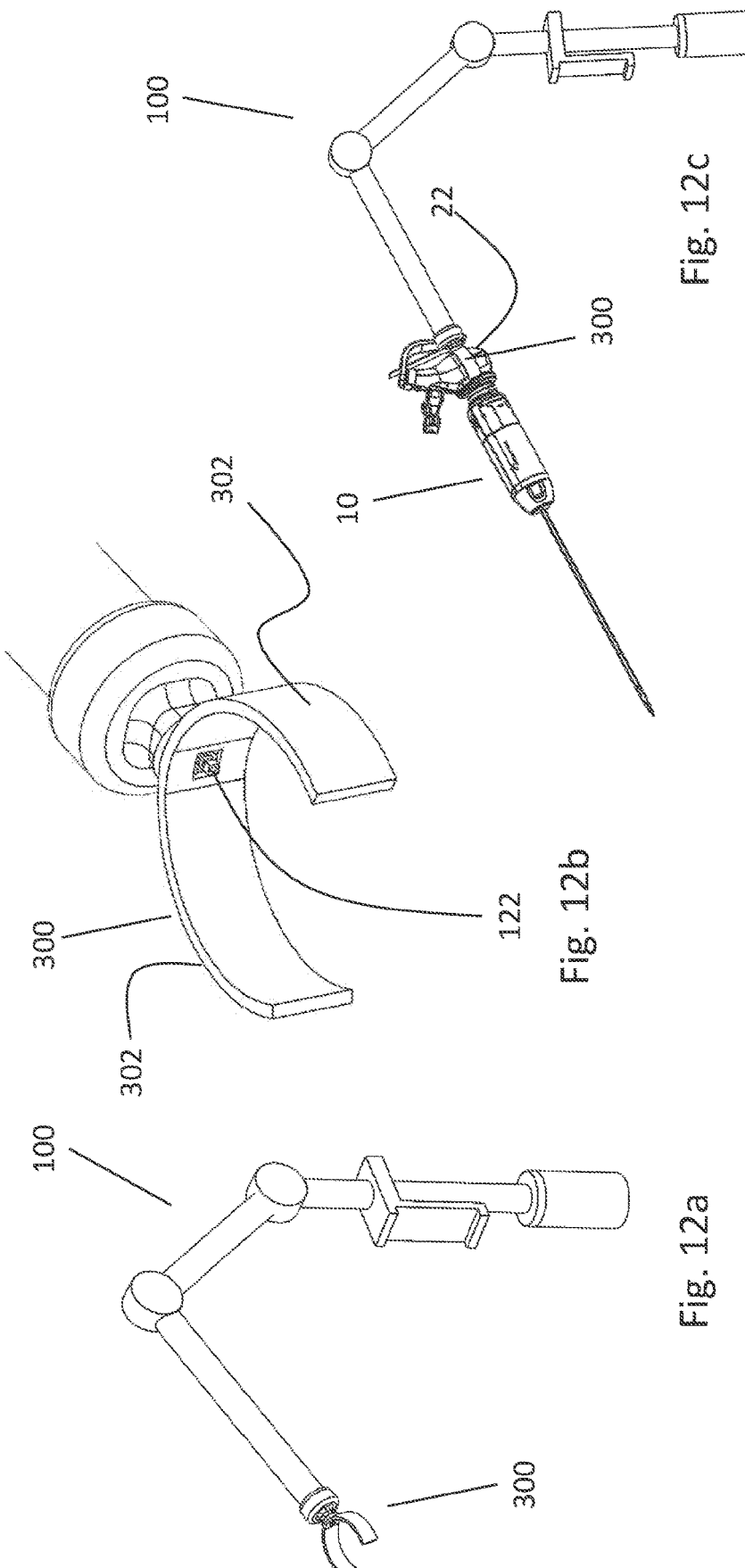
Figures 12D, 12E, 12F:
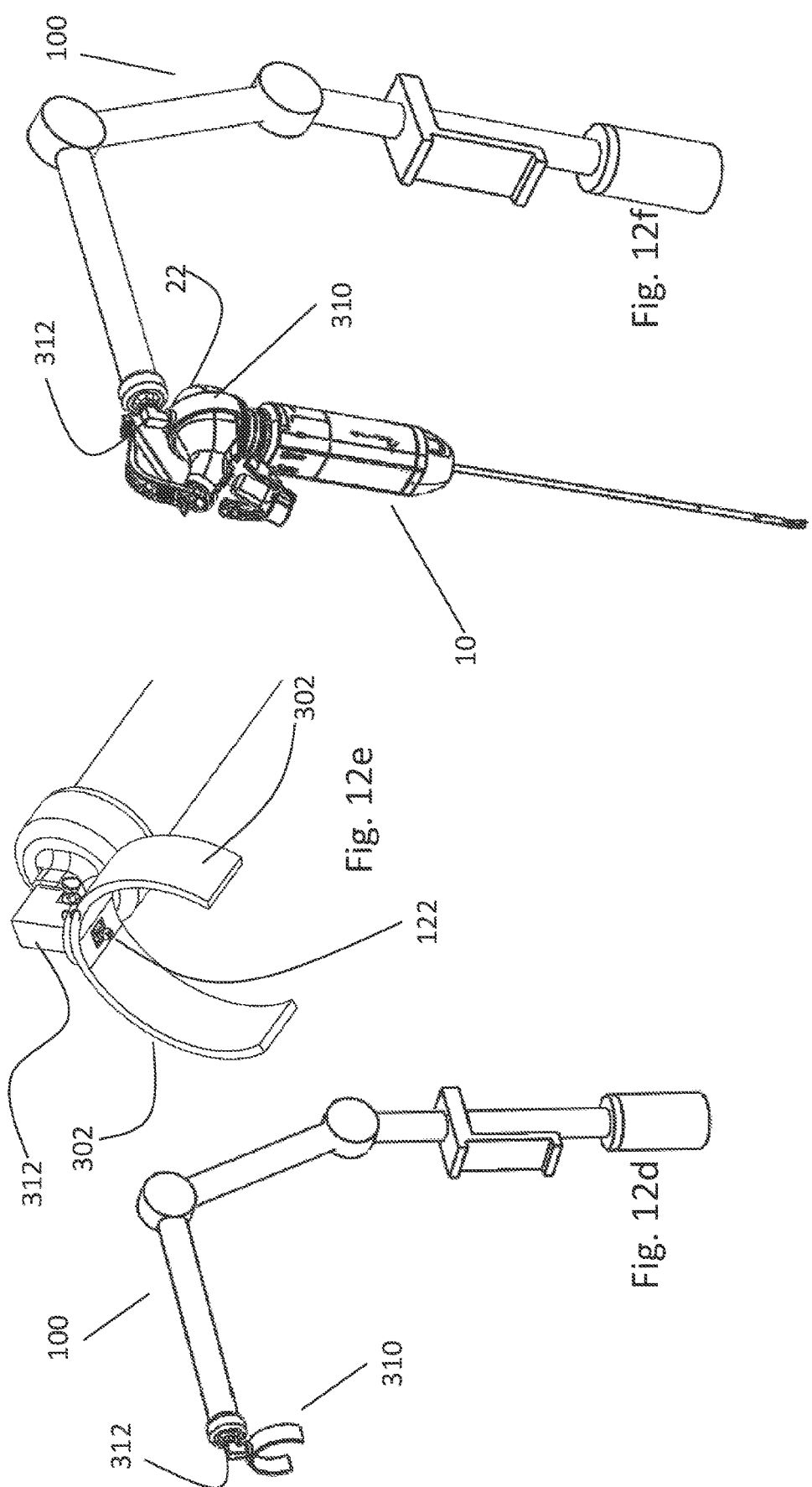

As is shown in FIGS. 12A-C, adapter 300 can be co-aligned with the center of rotation of interface 22 (as is described hereinabove with respect to FIGS. 3A-6). Adaptor can alternatively be connected to distal arm 110 via an angled connector 312 (FIGS. 12D-F).

Another option that can be used to lock interface 22 when robotic arm 100 is connected to device 10 utilizes an interface lockout mechanism of device 10. Device 10 can include a motorized braking mechanism that locks/unlocks interface 22 when used manually by a surgeon. Such a mechanism can be switched on when robotic arm 100 is connected to device 10 (over a drape). This locks the gimbal mechanism (at any desired position, e.g., center) of the palm interface and allows device 10 to be used with the robotic arm.

FIG. 7A illustrates manual positioning of device 10 by the surgeon hand 50 while holding the integrated interface 22. The surgeon may tilt device 10 to any desired orientation with respect to fulcrum point 60 as illustrated by orientation arrows 80, and slide the shaft of device 10 in and out through fulcrum point 60 in the direction of linear arrows 82.

FIGS. 7B-E illustrate remote control over device 10 by remote user interface 200 (hereinafter interface 200). In this configuration, integrated interface 22 serves as a passive coupler between robotic arm 100 and the body and the shaft 24 of device 10, allowing the positioning and orientation of device 10 by robotic arm 100.

Robotic control through interface 200 is affected as follows. Device 10 is connected to robotic arm 100 through adaptor 120 and rod 122, while interface 22 is deactivated and engaged (via rod 124) in a center position, changing the function of interface 22 to a passive gimbaled coupler, located at a known point at the end of the longitudinal axis of distal link 110 of robotic arm 100, as represented with center line 148 at FIG. 5.

Once device 10 is attached to robotic arm 100, sensors located at spherical base 136 serve as pitch and yaw measuring sensors for the combined control circuits (220, 222, 224) as is described below with reference to FIGS. 9A-10.

FIGS. 7B-C illustrate remote control over end effector positioning when device 10 is attached to robotic arm 100. It should be noted that the surgeon views the procedure through a 2D screen (FIG. 7F), and as such, the end effector positions are viewed as movements by directions left, right, up and down as is shown in FIG. 7F.

When the surgeon wishes to move end effector 26 of device 10 to the left (as indicated by arrow 62), while shaft 24 is positioned through fulcrum point 60, the surgeon moves the tip of the remote control 200 to the left (arrow 72) commanding robotic system 100 to tilt device 10 clock wise (CW) to the right with respect to fulcrum 60 thus rotating shaft 24 counter clockwise (CCW) around fulcrum 60 in direction 62 resulting in movement of tip 26 to the left.

As is shown in FIG. 7C, when the surgeon wishes to move end effector 26 of device 10 to the right (direction 64), the surgeon moves the tip of the remote control 200 to the right (arrow 74), commanding robotic system 100 to tilt device 10 CW to the left with respect to fulcrum 60 thus rotating shaft 24 around fulcrum 60 resulting in movement of tip 26 to the right.

FIGS. 7D-E show up and down remote control of end effector positioning while operating with robotic system.

When the surgeon wishes to move end effector 26 of device 10 down (arrow 66), the surgeon moves the tip of the remote control 200 down (arrow 76) as is shown in FIG. 7D commanding robotic system 100 to tilt device 10 up with respect to fulcrum 60, forcing tip 26 to move down.

When the surgeon wishes to move end effector 26 of device 10 up (arrow 68), the surgeon moves the tip of the remote control 200 up (arrow 78) as is shown in FIG. 7E, commanding robotic system 100 to tilt device 10 down with respect to fulcrum 68, forcing tip 26 to move up.

FIGS. 8A-B show in and out remote control of end effector 26 positioning while operating with robotic system.

When the surgeon wishes to move end effector 26 of device 10 in (arrow 84, FIG. 8A), the surgeon slides tip 210 of the remote control 200 away from remote control base 202 (arrow 94) commanding robotic system 100 to slide shaft 24 of device 10 through fulcrum 60 into the patient body, moving tip 26 deeper within the body cavity.

When the surgeon wishes to move end effector 26 of device 10 out (arrow 86 FIG. 8B), the surgeon slides the tip of the remote control 200 toward remote control base 202 (arrow 96) commanding robotic system 100 to slide shaft 24 and tip 26 out of the body cavity.

FIGS. 9A-B illustrate the processing steps for controlling the surgical instrument when movement is actuated via user interface 22 (FIG. 9A) and remote control 200 and robotic arm 100 (FIG. 9B).

FIG. 9A is a flowchart explaining the control of end effector 26 of device 10 using interface 22. In order to operate with device 10, the surgeon holds device 10 by user interface 22 while he positions end effector 26 in the patient body sliding the shaft trough the incision and use the incision as a fulcrum point. While the surgeon moves the device to the desired position, the surgeon may control the end effector orientation by tilting interface 22 with respect to the body 16 of device 10. The orientation of the articulation is controlled by orientation sensors located at user interface 22 (CI). The central processing unit uses readings from the orientation sensors to calculate the desired articulation angles and translate them to commands to the motors that operate articulation of end effector 26. The control of the end effector mechanism is performed by a similar control flow. For example, if the end effector is a grasper then pressing and releasing the pedals of the fingers interface controls the jaws open and close movement and rotating the pedals controls the rotation of the grasper jaws.

FIG. 9B is a flowchart explaining the control of distal connector 120 of robotic arm 100 using remote controller 150 (which will be replaced by remote control 200 customized for control the robotic surgery system 70). In order to move the tip of adapter 120 located at the distal end of the robotic arm 100, to a desired position, the user moves the handle of remote controller 150 in a desired direction or to a desired position (depending on the algorithm used for control). The central processing unit of the robotic arm 100 calculates the commands needed to bring the tip of distal adapter 120 to the desired position and translates them to commands for the motors resulting in tip movement to a desired position.

FIG. 10 is a flowchart outlining signals and controls processed by central processing unit 220 of a surgical robotic system 70. When interface 22 of device 10 is connected to robotic arm 100, both limit switches 122 and 140 are depressed indicating to processing unit 220 that interface 22 is converted into a passive gimbal that measures the orientation of body 16 of device 10 relative to the distal link 110 of robotic arm 100. Central processing unit 220 can then calculate the orientation of shaft 14 and the position of end effector 26 since the geometrical dimension of device 10 are known.

When lever 142 is depressed the control circuit of device 10 does not use readings from the pitch and yaw sensors of interface 22 of device 10 as inputs for controlling articulation and also disables the reading from sensors of the fingers interface 56. Until both limit switches 122 and 142 are released, commands controlling articulation and end effector movement are generated by remote control 200 only.

When device 10 is moved by robotic arm 100, it is essential to ensure that the movement of device 10 will be safe and will not harm the patient by, for example, applying forces to the incision site.

Thus, the present system enables the surgeon to calibrate the incision point location with respect to end effector 26 and shaft 24 by inserting end effector 26 into through the trocar. When end effector 26 is located in the rotation point of the trocar, the surgeon presses a calibration button/Since the dimensions of the segments and joints of robotic arm 100 and the angles between segments are known, and since the dimensions of device 10 and its orientation measured by pitch and yaw sensors of interface 22 are known, the exact location of the incision point can be calculated, and the fulcrum point may be determined, enabling the control circuit of system 70 to orient and slide device 10 safely with respect to the incision site. If the calibration process was performed incorrectly and was not accurate interface 22 (serving as a passive coupler), will also serve as a safety mechanism and may compensate for an inaccurate calibration process.

Following initial calibration, recalibration can be continuously executed as device 10 is moved by robotic arm 100. When the control circuit of system 70 moves device 10 in a calculated path, the control circuit calculates also the angles of user interface 22. Also a continuous online calibration may be executed: when a path is executed, the control circuit may read the signals from the pitch and yaw sensors of user interface 22 and compare them to pre-calculated values. If the error is bigger than a desired value, the control system calculates new values for the incision point that will reduce the error to an acceptable value.

The same correction process may be executed when the shaft slides in and out through the incision site.

Adding an inertial measurement unit (IMU) component to device 10 may serve also for reducing positioning errors and ensuring smooth movement of device 10.

User interface 22 may also serve as a safety mechanism by comparing the signals acquired from user interface 22 to the pre-calculated values of the sensors. For example, if the end effector collides unexpectedly with tissue in the body cavity then the robotic arm will continue its pre-determined calculated path while the measured signals from user interface 22 will not match the these pre-calculated values. The control system will calculate and watch the increasing difference between the measured values and the expected pre-calculated values until reaching an unacceptable threshold leading to a stop or slow down in movement.

A combination of readings from IMU connected to device 10 and signals from the sensors of interface 22 can be also used to increase the level of safety of system 70 in the same manner as described above.

When using more than one robotic arm 100 (each attached to a dedicated device 10), a second calibration process may be executed following calibration of each arm 100. The second calibration process will be used by the central control system to avoid collisions between robotic arms 100 or collision between shafts of devices 10.

In order to execute the second calibration process the user can attach the end effectors 26 of two devices 10 to each other, and then press a second calibration button on control unit 200. Since the dimensions of both robotic arms 100 are known, the origin of each robotic arm 100 with respect to the other robotic arm 100 may be calculated. The second calibration process allows the control system to calculate the spatial location of each link, device, and shaft of each robotic system and to eliminate collision therebetween. It should be noted that the user may execute the two calibrations processes in a reversed order, i.e., first the calibration between the robotic arms and then the incision point calibration. Also, the calibration between the robotic arms may be done outside or inside the patient body and repeated whenever necessary.

Interface 200 may communicate with device 10 and robotic arm 100 through a physical wire or by wireless connection (e.g., Bluetooth, Wi-Fi or a dedicated RF protocol).

Interface 200 includes a base 202 connectable to an object or to the surgeon (e.g., at belt). Base 202 is connected to a first arm 204 through a gimbaled joint 206. A second arm 208 is telescopically connected to first arm 204 and can move forward/back and rotate with respect thereto. The distal end of second arm 208 is connected to a finger interface 210 via hinge 211 that allows pivoting of finger interface 210 with respect to second arm 208. Finger interface 210 can be used to rotate an effector end (e.g. grasper) via rotation of arm 208 with respect to arm 204, to open/close grasper jaws via the open and close function of paddles 213 and deflect shaft 14 via movement at hinge 211.

Interface 200 provides control over robotic arm 100 movement via movement of first arm 204 with respect to base 202 (through gimbaled joint 206). As is shown in FIGS. 7B-D, tilt left of arm 204 with respect to base 202 translates to tilt right of device 10 (as actuated by robotic arm 100), while tilt right of arm 204 with respect to base 202 translates to tilt left of device 10 (as actuated by robotic arm 100) Likewise tilt up of arm 204 with respect to base 202 translates to tilt back of device 10 (as actuated by robotic arm 100) and tilt down of arm 204 with respect to base 202 translates to tilt forward of device 10 (as actuated by robotic arm 100). Such control over the position of device 10 is similar to the control over a surgical device used in an open procedure where the end effector of the surgical device moves with the same direction of the hand of the surgeon.

FIG. 11 illustrates a typical setup using three system 70 in a laparoscopic surgery.

When surgeon 3 decides to use system 70, robotic arms 10*a-c* may be positioned via carts next to surgical table 70 and clamped to rails 71 located at the side of surgical table 7. Handheld devices 10*a-b* are then connected to robotic arms 100*a-b* and laparoscopic camera can be connected to robotic arm 100*c*.

Devices 10*a-b* are inserted through incisions 60*a-b* respectively and laparoscope 11 is inserted through incision 60*c*.

A two steps calibration process is executed for devices 10*a-b* and laparoscope 11, as is described above. In order to perform the surgical procedure, surgeon 3 holds the fingers interfaces of remote user interfaces 200*a-b* to simultaneously control both handheld devices 10*a-b*. To position the laparoscopic camera, surgeon 3 switches control from one of interfaces 200*a* or 200*b* to the camera control. The laparoscopic camera may be also controlled by assistant (not shown) that uses an additional remote user interface 200. At any point in the procedure, the surgeon and staff may disconnect one of devices 10*a-c* and another surgeon or assistant can manually operate one or more of devices 10*a-c*, while the surgeon remotely controls devices connected to robotic arms 100*a-c*. Since robotic arms 100*a-c* include safety protocols (As is described above), there is no potential risk for the assistant that works near robotic arms that are remotely controlled. In addition, any of robotic arms 100*a-c*, can be operated by a surgeon which is not present in the operating room (e.g., teleoperating). As the procedure continues the handheld devices may be re-connected to the robotic arms and if no setup changes were introduced, no additional calibration is needed.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A surgical system comprising:

a surgical device having an end effector and an integrated user interface controllable by a hand of a surgeon and being for operating said end effector through a drive unit attached to said integrated user interface;

an adaptor for connecting said integrated user interface of said surgical device to a robotic arm, wherein said connecting enables remote operation of said surgical device; and a control unit for remotely operating said surgical device and said robotic arm when connected via said adaptor, wherein said control unit operates said surgical device through said drive unit attached to said integrated user interface and spatially maneuvers said surgical device via said robotic arm and further wherein said integrated user interface provides orientation information for said robotic arm when said adaptor connects said integrated user interface to said robotic arm.

2. The system of claim 1, wherein said adaptor is connectable to or integrated with said robotic arm.

3. The system of claim 2, wherein said adaptor includes a rod that fits into a slot in said integrated user interface, said slot being in a center of rotation of said integrated user interface.

4. The system of claim 3, wherein fitting said rod into said slot activates a switch for transferring control of said integrated user interface to said control unit.

5. The system of claim 1, wherein said adaptor externally connects to said integrated user interface.

6. The system of claim 5, wherein said adaptor is configured for attachment to said integrated user interface over a sterile drape.

7. The system of claim 1, wherein when said adaptor is connected to said surgical device said integrated user interface is mechanically locked.

* * * * *